United States Patent
Yang et al.

(10) Patent No.: US 11,338,262 B2
(45) Date of Patent: May 24, 2022

(54) METHOD FOR IMPROVING REACTION YIELD

(71) Applicant: NOVASHIN CO., LTD., Beijing (CN)

(72) Inventors: Jianchun Yang, Beijing (CN); Kai Han, Beijing (CN); Dongmei Yang, Beijing (CN)

(73) Assignee: NOVASHIN CO., LTD., Beijing (CN)

(*) Notice: Subject to any disclaimer, the term of this patent is extended or adjusted under 35 U.S.C. 154(b) by 0 days.

(21) Appl. No.: 17/258,720

(22) PCT Filed: Mar. 11, 2020

(86) PCT No.: PCT/CN2020/078729
§ 371 (c)(1),
(2) Date: Jan. 7, 2021

(87) PCT Pub. No.: WO2020/182138
PCT Pub. Date: Sep. 17, 2020

(65) Prior Publication Data
US 2021/0283564 A1  Sep. 16, 2021

(30) Foreign Application Priority Data
Mar. 11, 2019 (CN) .......................... 201910181451.2

(51) Int. Cl.
*B01J 8/02* (2006.01)
*B01J 8/06* (2006.01)

(52) U.S. Cl.
CPC ............ *B01J 8/067* (2013.01); *B01J 8/0242* (2013.01); *B01J 2208/00362* (2013.01); *B01J 2208/00371* (2013.01); *B01J 2208/00557* (2013.01)

(58) Field of Classification Search
CPC ... B01J 8/067; B01J 8/06; B01J 8/0285; B01J 8/0242; B01J 8/0496; B01J 2208/00557;
(Continued)

(56) References Cited

U.S. PATENT DOCUMENTS

| | | | | |
|---|---|---|---|---|
| 3,227,527 | A | * | 1/1966 | Heinze ................... B01J 8/0285 422/207 |
| 4,044,027 | A | * | 8/1977 | Anderson .................. B01J 8/06 549/259 |

(Continued)

FOREIGN PATENT DOCUMENTS

| CN | 1031697 A | 3/1989 |
|---|---|---|
| CN | 1697802 A | 11/2005 |

(Continued)

*Primary Examiner* — Lessanework Seifu
(74) *Attorney, Agent, or Firm* — Novick, Kim & Lee, PLLC; Allen Xue

(57) ABSTRACT

In a catalytic reaction, after a reaction product leaves a catalyst bed, an inert substance with a low temperature is sprayed, and through heat absorption and vaporization processes of the inert substance, the temperature of the reaction product drops rapidly when staying in a catalyst cushion layer at a discharge end of a fixed bed reactor, or in a space formed by the catalyst cushion layer at the discharge end of the fixed bed reactor and a reactor head, or in a space formed by a tube plate at the discharge end of the fixed bed reactor and the reactor head. The residence time of the reaction product is shortened due to the entrance of the inert substance in a gaseous state.

8 Claims, 2 Drawing Sheets

(58) Field of Classification Search
CPC ...... B01J 2208/00371; B01J 2208/0362; B01J 2208/00336
See application file for complete search history.

(56) References Cited

U.S. PATENT DOCUMENTS

| | | | |
|---|---|---|---|
| 6,544,924 B1 | 4/2003 | Jackson et al. | |
| 2006/0149114 A1* | 7/2006 | Colman | ............. B01J 8/0496 585/658 |

FOREIGN PATENT DOCUMENTS

| | | |
|---|---|---|
| CN | 100462349 C | 2/2009 |
| CN | 101990457 A | 3/2011 |
| CN | 102671580 A | 9/2012 |
| CN | 202666813 U | 1/2013 |
| JP | S4954317 A | 5/1974 |
| JP | H05125010 A | 5/1993 |
| JP | 6217579 B2 | 10/2017 |

* cited by examiner

METHOD FOR IMPROVING REACTION YIELD

CROSS-REFERENCE TO RELATED APPLICATIONS

The application is a U.S. national phase entry of International Application No. PCT/CN2020/078729, filed on Mar. 11, 2020, which claims the priority of the prior Chinese Application No. 201910181451.2 submitted to China National Intellectual Property Administration on Mar. 11, 2019, which is entitled "A method for improving reaction yield", the entire content of the prior application is incorporated herein by reference.

FIELD OF THE INVENTION

The application belongs to the field of chemical industrial production preparation technology, in particularly relates to a method for improving reaction yield, especially a method for improving reaction yield of heat-sensitive reaction product.

BACKGROUND OF THE INVENTION

The fixed bed catalytic reactor has a faster reaction rate. It can get larger output with smaller amount of catalyst and smaller reactor volume. The catalyst is not prone to wear and may service over a long period of time. Due to the residence time of the fixed bed catalytic reactor can be strictly controlled and the temperature distribution can be adjusted appropriately, so it has the advantage of high selectivity and relatively high conversion rate etc. Therefore, fixed bed catalytic reactors are widely used.

The reaction temperature of the fixed bed reactor is generally relatively high. In the space between the lower inert cushion under the fixed bed catalyst or the lower tube sheet of the multi-tube fixed bed reactor catalyst tube and the reactor heads, there are high concentration of the product, high temperature, long residence time of the product in the space. If the temperature can not be reduced rapidly in time and the product can not be removed from the space to quenche, the heat-sensitive reaction products are prone to undergo side reactions such as decomposition or self-polymerization. It is of great significance for improving the yield and selectivity of products for how to quickly remove the reaction product from the reactor and cool down, and thus reduce the decomposition and side reactions.

Chinese patent document CN101990457A discloses a tubular reactor. The reactor comprises, at the outlet, the outlet housing and at least one insert located in the outlet space defined by the outlet. The insert(s) restricted the outlet space. The space volume of such outlet space is reduced relatives to the outlet space defined by the outlet itself, and the outlet space, whose volume is reduced, communicated with the outlet end of the reaction tube. The volume of the outlet space with such arrangement is reduced by about 40%. This tubular reactor can be used for producing EO from ethylene by oxidation. When the tubular reactor is operated, the volume of the outlet space is reduced by about 40% due to the insert in the space of the outlet. In turn, the residence time of the material in the outlet head space is reduced by 40%, but the temperature of the material has not decreased significantly. Even the residence time is reduced, the side reactions such as decomposition or self-polymerization will still occur for the heat-sensitive reaction products due to that the temperature has not decreased.

In order to prevent the reaction product from retention in the gap on the outlet side of the reaction tube, Chinese patent document CN100462349C discloses a reactor, which sets a deflector in the tube sheet on the outlet side in order to avoid reaction products retention in the gap on the outlet side of the reaction tube. This reactor also reduces the problem of retention of reaction products on the outlet side of the reaction tube, but there is not much improvement in reducing the residence time and the temperature of the reaction product in the space on the outlet side.

Japanese Patent Document JP-A-5-125010 proposes to reduce the residence time of the reaction gas in the outlet part of the outlet side of the reaction tube by making the volume of the outlet portion of the reaction gas in the outlet side of the oxidation reaction tube smaller than the inlet portion of the raw material gas, thus inhibit the production of by-product diones. Japanese Patent Document JP-B-62-17579 proposes to configure a cooling section which includes the filling layer of solid inert material that are located close to the downstream side of the catalyst in the area of the reaction zone. However, when the reaction gas is cooled down, there are shortcomings, for example, heavy impurities with high boiling point present in the gas condense and plug the reactor etc.

Ethylenically unsaturated acids and their esters are important chemical raw materials, such as acrylic acid (abbreviation: AA) and its esters. There are many industrial production methods for producing ethylenically unsaturated acid and its ester. For example, the process for preparing ethylenic unsaturated acid and its ester by catalyzing the condensation reaction between saturated alkyl acids and their esters and formaldehyde with an alkali metal-impregnated catalyst having silica gel and the like as a support.

The reaction process is as follows:

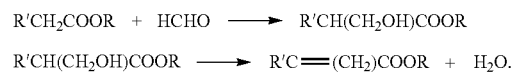

The side reaction process is as follows:

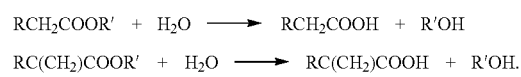

US Patent Document U.S. Pat. No. 6,544,924 discloses a method and a catalyst used for producing ethylenically unsaturated acid or ester by the catalytic reaction of alkanoic acids or esters, especially methyl propionate with formaldehyde. The catalyst comprises 1-10% (by weight) alkali metal, especially porous high-surface area silica of cesium. It can be seen from the data of patent implementation examples that the shorter the residence time of the reactants is, the selectivity is higher.

Due to the thermal instability of the product ethylenically unsaturated acids and their esters, they are prone to polymerize and decompose by heat. Therefore, it is necessary to cool down the product ethylenically unsaturated acids and their esters as soon as possible and quickly move out of the high temperature zone, thus ensure the high selectivity of target products and reduce material loss.

However, there is no better way that can solved the problem of the long residence time of the reaction product in the space of the outlet side of the reactor and the overly high reaction product temperature cause the side reactions which in turn leads to a reduction in the yield of the reaction products.

SUMMERY OF THE INVENTION

In order to improve the deficiencies of the prior art, the object of the present invention is to provide a method for improving the reaction yield, it especially relates to a method for improving the reaction yield of heat-sensitive reaction products. The method can solve the problem of the adverse effects on reaction products due to the long residence time of the reaction product in the space on the outlet side of the reactor and the high reaction product temperature etc. The method can effectively improve the yield of the reaction.

The object of the invention is solved by the following technical solutions:

A method for improving the reaction yield, especially a method for improving the reaction yield of heat-sensitive reaction products, the method comprises:

feeding reaction raw materials into a fixed bed reactor; the reaction raw materials flow through a catalyst bed to obtain reaction products; the reaction products pass through a catalyst cushion at a discharge end of the fixed bed reactor and then a space which is formed by the catalyst cushion and a reactor head, thereafter leave the reactor; or the reaction products pass through a space which is formed by a tube sheet at the discharge end of the fixed bed reactor and a fixed bed reactor head, thereafter leave the reactor; at this time, performing at least one of the following operations (i), (ii) and (iii):

(i) injecting an inert substance into the catalyst cushion at the discharge end of the fixed bed reactor;

(ii) injecting an inert substance into the space which is formed by the catalyst cushion at the discharge end of the fixed bed reactor and the reactor head;

(iii) injecting an inert substance into the space which is formed by the tube sheet at the discharge end of the fixed bed reactor and the reactor head.

According to the invention, "inert" in said inert substance means the substance maintains inert under the operating conditions of the fixed bed reactor and does not undergo chemical reactions with the reaction raw materials and reaction products.

According to the invention, the reaction raw material is preferably a gas.

According to the invention, the inert substance is at least one of a gas or a liquid that can be vaporized after being heated.

Exemplarily, the inert substance is nitrogen, helium, argon, carbon dioxide; water; oxygenated organics with a carbon number less than or equal to 10; nitrogenous organics with a carbon number less than or equal to 10; naphthene with a carbon number less than or equal to 12; alkanes with a carbon number less than or equal to 12; aromatics with a carbon number less than or equal to 10; or a mixture of at least two of them.

Preferably, the inert substance is selected from at least one of the group consisting of nitrogen, helium, argon, carbon dioxide, water, $C_6$-$C_8$ alkane, $C_6$-$C_8$ aromatic, $C_1$-$C_4$ alcohol, $C_1$-$C_4$ acid, $C_2$-$C_4$ nitrile and $C_2$-$C_4$ ester. Further preferably, the inert substance is selected from at least one of the group consisting of nitrogen, helium, argon, carbon dioxide, hexane, heptane, benzene, toluene, xylene, methanol, ethanol, propionic acid, methyl propionate, acetonitrile and water.

According to the invention, the fixed bed reactor is a conventional fixed bed reactor known in the art, exemplarily, the fixed bed reactor can be a tube bundle reactor or a single tube reactor, and the reactor has a head, and its specific structure can be seen in FIG. 1; the tube bundle reactor comprises a tube sheet and a head; the single tube reactor comprises a catalyst cushion and a head.

According to the invention, the inert substance is injected into the reactor through a nozzle; optionally, the nozzle is provided with nozzle hole(s); the nozzle refers to a tubular component that delivers an inert substance from outside of the reactor into inside of the reactor; the nozzle is arranged in the catalyst cushion at the discharge end of the fixed bed reactor, and/or is arranged in the space which is formed by the catalyst cushion at the discharge end of the fixed bed reactor and the reactor head, or is arranged in the space which is formed by the tube sheet at the discharge end of the fixed bed reactor and the reactor head. The specific structure can be seen in FIG. 1, FIG. 1 shows a tube bundle reactor (a), a nozzle is arranged in the space which is formed by the tube sheet at the discharge end of the fixed bed reactor and the reactor head; FIG. 1 shows a single tube reactor (b), a nozzle is arranged in the catalyst cushion at the discharge end of the fixed bed reactor; FIG. 1 shows a single tube reactor (c), a nozzle is arranged in the space which is formed by the catalyst cushion at the discharge end of the fixed bed reactor and the reactor head; with regard to the single tube reactor, the nozzle can also be arranged both in the catalyst cushion at the discharge end of the fixed bed reactor and in the space which is formed by the catalyst cushion at the discharge end of the fixed bed reactor and the reactor head (not shown in figure).

According to the invention, the amount of the inert material injected is 0.1-5 times the weight of the feed amount of the fixed bed reactor, preferably 0.5-2 times weight, for example, 0.1 times weight, 0.2 times weight, 0.5 times weight, 0.8 times weight, 1 time weight, 1.5 times weight, 2 times weight, 3 times weight, 4 times weight or 5 times weight, wherein, the feed amount of the fixed bed reactor refers to the total mass of the reaction raw materials.

In the present invention, because of the injection of the inert substances, the inert substances will absorb a large amount of heat for temperature increase or vaporization, such that the outflow reaction products (especially the heat-sensitive reaction products) cool down quickly, and a large volume of space (such as the space in the catalyst cushion, and/or the space which is formed by the catalyst cushion at the discharge end of the fixed bed reactor and the reactor head, or the space which is formed by the tube sheet at the discharge end of the fixed bed reactor and the reactor head) is occupied at the same time, such that the reaction products are accelerated out of the fixed bed reactor, which effectively reduces the occurrence of heat-sensitive side reactions of the reaction products; thus achieves a significant increase in reaction yield.

According to the invention, the reaction products, especially the heat-sensitive reaction products, can be ethylenically unsaturated acids and their esters, such as vinyl acetate, acrylic acid, methacrylic acid, acrylate, methacrylate (such as methyl methacrylate) etc. The reaction products can also be ethylenically unsaturated aldehyde, such as acrolein, methacrolein, etc., and also can be the olefins, such as propylene, isobutylene, butadiene and styrene compounds, etc.; the reaction products also can be epoxides, such as ethylene oxide, propylene oxide, etc., and unsaturated acid anhydrides, such as maleic anhydride etc.

According to the invention, the reaction raw materials may be raw materials for preparing the above reaction products, including at least one of olefins, alkanes, aromatic hydrocarbons, carboxylic acids, carboxylic acid esters, aldehydes, alcohols, etc., specifically comprise at least one of ethylene, propylene, isobutylene, propane, butane, isobutane, acetic acid, propionic acid, methyl acetate, methyl propionate, formaldehyde, vinylaldehyde, acrolein, methacrolein, methanol, butene-1, phenylethanol, ethylbenzene, etc., the reaction raw material gas may be obtained by heating and vaporizing the reaction raw materials through a vaporizer.

According to the invention, the catalyst which is filled in the fixed bed reactor can be any catalyst known in the art to use the above reaction raw materials to prepare the above reaction products, especially the heat-sensitive reaction products.

Exemplarily, when the reaction product is ethylene oxide, the reaction raw materials comprise ethylene and oxygen, optionally can also comprise methane or nitrogen. The catalyst is selected from silver catalyst.

Exemplarily, when the reaction product is propylene oxide, the reaction raw materials comprise propylene and oxygen. The catalyst is selected from silver catalyst.

Exemplarily, when the reaction product is acrylic acid, the reaction raw materials comprise acrolein and oxygen, and also comprise the water vapor. The catalyst is selected from molybdenum-vanadium catalyst.

Exemplarily, when the reaction product is methacrylic acid, the reaction raw materials comprise methacrolein and oxygen, and comprise water vapor. The catalyst is selected from molybdenum-vanadium catalyst.

Exemplarily, when the reaction product is methacrylic acid or methyl methacrylate, the reaction raw materials comprise propionic acid or methyl propionate and formaldehyde, optionally can also comprise methanol and/or nitrogen. The catalyst is selected from the silica catalyst containing cesium.

Exemplarily, when the reaction product is acrylic or acrylate, the reaction raw materials comprise acetic acid or methyl acetate and formaldehyde, optionally can also comprise methanol and/or nitrogen. The catalyst is selected from the silica catalyst containing cesium.

Exemplarily, when the reaction product is acrolein, the reaction raw materials comprise propylene or propane and oxygen, and comprise water vapor. The catalyst is selected from molybdenum-bismuth catalyst.

Exemplarily, when the reaction product is methacrolein, the reaction raw materials comprise isobutene or isobutane and oxygen, and comprise water vapor. The catalyst is selected from molybdenum-bismuth catalyst.

Exemplarily, when the reaction product is vinyl acetate, the reaction raw materials comprise ethylene, acetic acid, and oxygen. The catalyst is selected from supported palladium catalyst.

Exemplarily, when the reaction product is propylene or isobutylene, the reaction raw material comprises propane or isobutane. The catalyst is selected from noble metal dehydrogenation catalyst.

Exemplarily, when the reaction product is styrene, the reaction raw material is ethylbenzene. The catalyst is selected from the catalyst containing iron and potassium.

Exemplarily, when the reaction product is styrene, the reaction raw material at least contains phenylethanol. The catalyst is selected from alumina dehydration catalyst.

Exemplarily, when the reaction product is butadiene, the reaction raw materials comprise butene-1 or butane and oxygen, and comprise water vapor. The catalyst is selected from the catalyst containing iron.

Exemplarily, when the reaction product is maleic anhydride, the reaction raw materials comprise butane and oxygen, and comprise water vapor. The catalyst is selected from vanadium-molybdenum catalyst.

According to the invention, the temperature of the reaction is slightly differs from each other due to the specific reaction raw materials and the prepared reaction products. Exemplarily, temperature of the reaction is adjustable in the range from 240° C. to 700° C.; after being cooled by the inert substance, the temperature of the reaction products which flow out of the fixed bed reactor can be reduced to 50-250° C.

According to the invention, the heat released or absorbed by the reaction is introduced in or removed out according to conventional methods. Exemplarily, such as during the preparation of acrolein by the oxidation of propylene, the reaction will release a large amount of heat, the released heat will be discharged through the molten salt filled outside the catalyst tube to maintain the reaction under the isothermal conditions.

The beneficial effects of the present invention:

The invention provides a method for improving the reaction yield, especially a method for improving reaction yield of heat-sensitive reaction product. Using the method of the present invention, after the reaction products leave the catalyst bed, by spraying low temperature inert substance, during the endothermic and/or vaporization of the inert substances, the reaction products remaining in the catalyst cushion at the discharge end of fixed bed reactor, and/or the space which is formed by the catalyst cushion at the discharge end of the fixed bed reactor and the reactor head, or the space which is formed by the tube sheet at the discharge end of the fixed bed reactor and the reactor head undergo rapidly temperature drop; meanwhile, due to the introduction of the inert substances, the residence time of the reaction products in the catalyst cushion at the discharge end of the reactor or the space which is formed by the catalyst cushion at the discharge end of the fixed bed reactor and the reactor head or the space which is formed by the tube sheet at the discharge end of the fixed bed reactor and the reactor head is significantly reduced, which avoid the phenomenon of increased by-products caused by long-time residence at high temperature; thus the reaction yield is significantly improved.

DETAILED DESCRIPTION OF THE INVENTION

Figure 1:
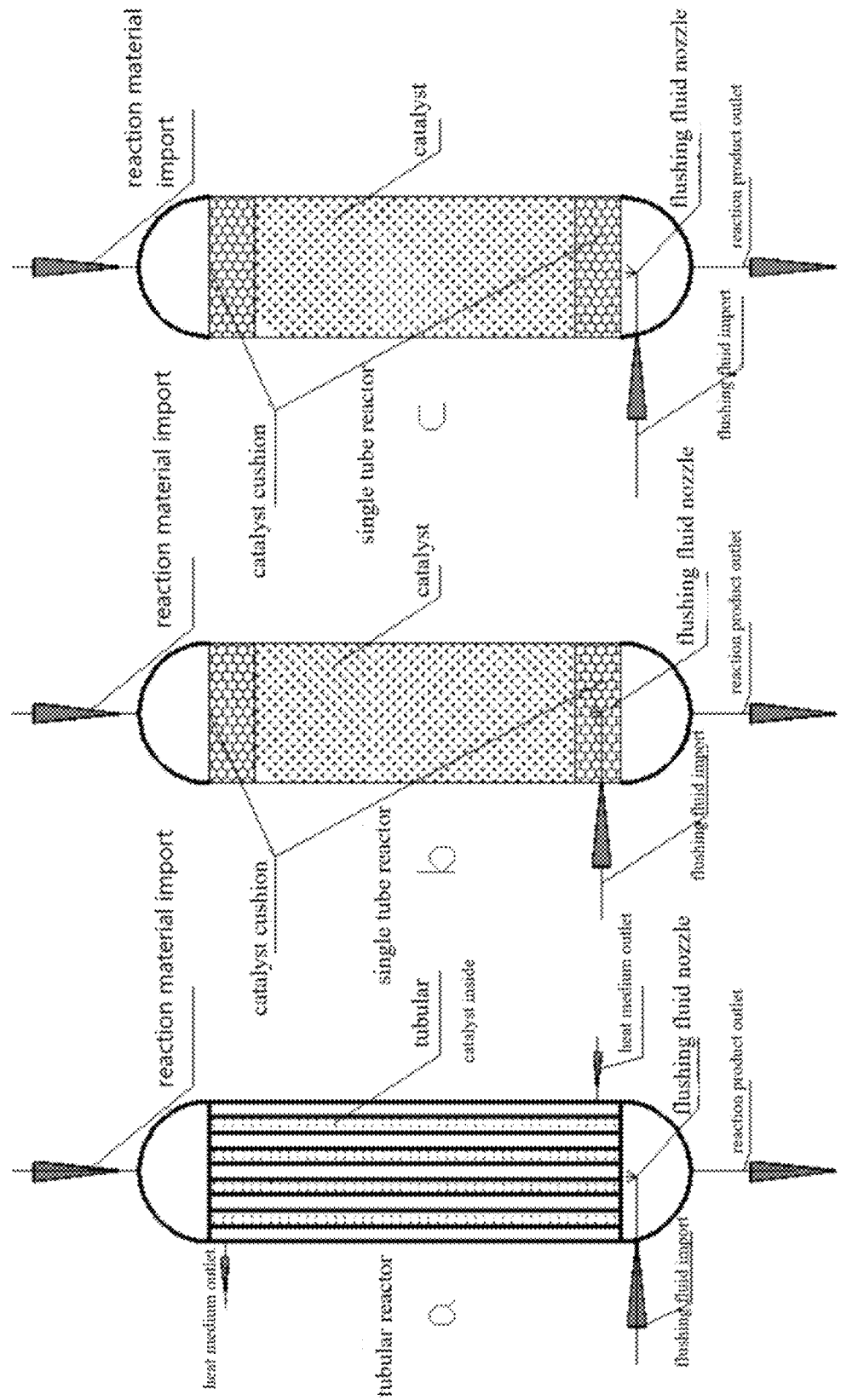
FIG. 1 is a schematic structural diagram of a fixed bed reactor according to the present invention.

The present invention will be further illustrated with reference to the specific examples below. It should be understood that the following examples are only used to illustrate the present invention, but are not intended to limit the scope of the present invention. In addition, it should also be understood that after reading the contents of the present invention, those skilled in the art can make various changes or modifications to the present invention, and these equivalent forms also fall within the scope defined by the present invention.

Unless otherwise specified, the experimental methods used in the following examples are conventional methods; unless otherwise specified, the reagents and materials used in the following examples can be obtained from commercial sources.

The analysis of propionic acid, methyl propionate, methanol, methacrylic acid and methyl methacrylate are carried out on the Agilent GC7820 with FID detector, DB-FFAP (30 m×0.53 mm×1 μm) capillary column, n-heptane as internal standard; exhaust gas is analyzed via online mass spectrometry model Extreme MAX300. The analysis of formaldehyde in raw materials and products is carried out by chemical titration; the water in raw materials and products are analyzed by Karl-Fischer method.

Conversion of methyl propionate (mol)=the amount of methyl propionate reacted (mol)/the amount of methyl propionate supplied (mol)×100%

Selectivity of propionic acid (mol %)=the amount of propionic acid produced (mol)/the amount of methyl propionate reacted (mol)×100%

Selectivity of methacrylic acid (ester) (mol %)=the amount of methacrylic acid (ester) produced (mol)/the amount of methyl propionate reacted (mol)×100%

Yield of methacrylic acid (ester) (mol %)=conversion of methyl propionate (mol %)×the selectivity of methacrylic acid (ester) (mol %)

The raw materials: methyl propionate, formaldehyde, and methanol, wherein, the molar ratio of methyl propionate and formaldehyde is 20:1-1:20. The molar ratio of methanol and formaldehyde is 0.1-1.5:1.

The catalyst is a supported alkali metal cesium silica gel catalyst, which has a loading of alkali metal cesium of 1-15 wt %; the catalyst has a specific surface area of 100-500 $m^2/g$, an average pore size of 10-17 nm, a pore volume of about 1 ml/g. The catalyst can be prepared by the following method: mixing and shaking the silica gel with alkali metal solution and modifier (such as 2 g/100 mol zirconium (weight of the metal)), and after immersing for 24 hours, drying to constant weight at 120° C., then calcined at 300-500° C. for 2-6 hours. For example, for the preparation of the catalyst, refers to U.S. Pat. No. 6,544,924.

The reactor is a single tube fixed bed reactor, the catalyst is packed in the middle of the fixed bed, bulk or granular inert packing such like ceramic, glass or quartz, etc locates above and below the catalyst to form the catalyst cushion.

Among them, formaldehyde can be formalin; or compounds that can produce formaldehyde by heating, such as paraformaldehyde, trioxane, methylal, etc.

Among them, the inert gas can also be mixed into the reaction materials, such as nitrogen, argon, helium etc., the dilute solvents such as alkanes, aromatics, etc. Nitrogen is preferred.

The mixed reaction materials and nitrogen are mixed and enter into the vaporizer to be heated and vaporized, and then enter the fixed bed reactor. The temperature of the vaporizer is 240-700° C., the catalyst bed is heated or removed by the medium outside the tube. In the fixed bed, the temperature is 240-400° C., the pressure is 0.1-1.0 MPag, preferably, the vaporizer temperature is 300° C., the fixed bed temperature is 350° C., the pressure is 0.1-0.5 MPag, the residence time is 1-100 s.

Example 1

Figure 2:
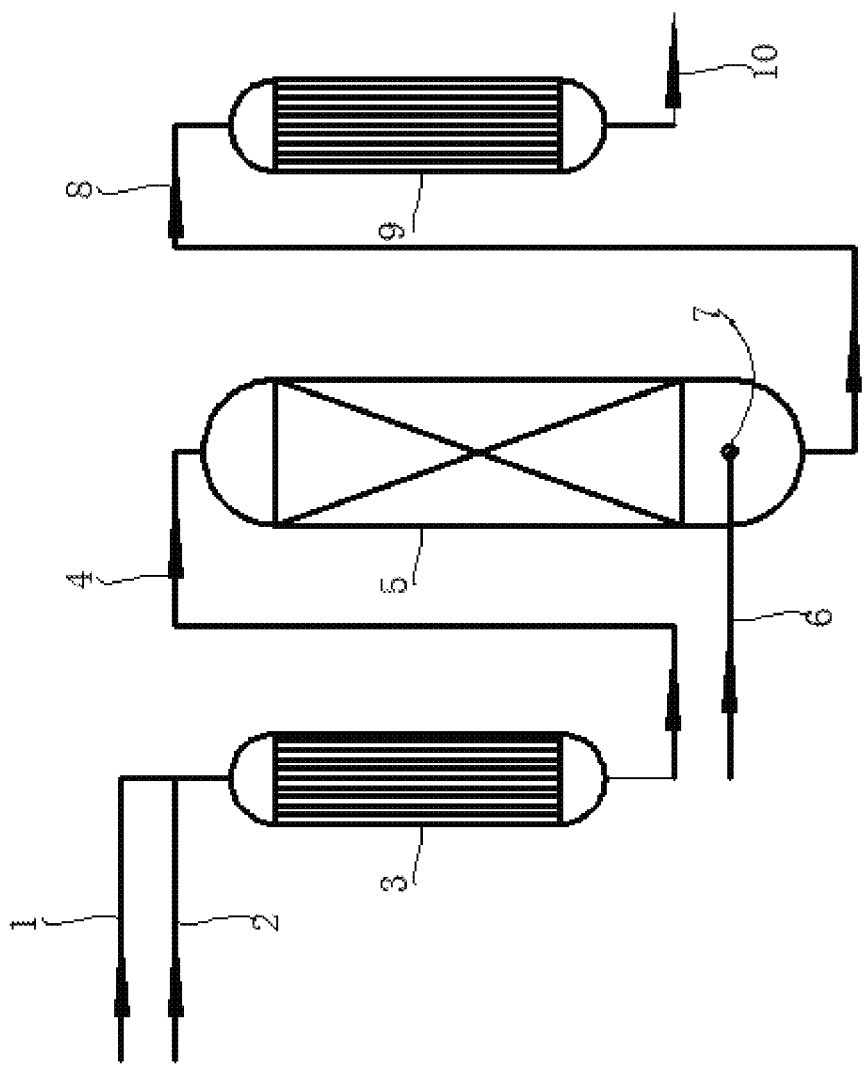
FIG. 2 is a flow chart of the reaction process according to the present invention.

FIG. 1 is a schematic structural diagram of a fixed bed reactor according to the present invention. FIG. 2 is a flow chart of the reaction process according to the present invention. As shown in FIG. 1 and FIG. 2, nitrogen 1 and mixed reactant 2 are mixed and enter into vaporizer 3, heated and vaporized, to obtain the heated mixture gas 4, the heated mixture gas 4 enters the reaction from the upper end of the fixed bed reactor 5, inert substances 6 enter into the catalyst cushion at the discharge end of the fixed bed from the lower part of the fixed bed (or into the space formed between the tube sheet at the discharge end of the fixed bed and the lower head of the fixed bed, or the space formed between the catalyst cushion at the discharge end of the fixed bed and the lower head of the fixed bed), and are sprayed into the fixed bed reactor from the inert substance nozzle 7; the reaction mixture 8 containing inert substances enters into the cooler 9 for cooling, the cooled gas-liquid mixture 10 contains products and unreacted raw materials.

Example 2

Preparing methyl methacrylate (MMA) by the process shown in Example 1 above

The methanol solution of formaldehyde: 96% (weight percentage, the same below) of paraformaldehyde and equal weight of methanol are mixed and heated to 100° C., keep warm and stirring for 4 hours, paraformaldehyde are all dissolved, the water content is 1% as measured.

15 g of catalyst crushed to 1 mm in size into the fixed bed reactor. 100 ml/min (standard condition) nitrogen is introduced through the vaporizer, which is set at 300° C. After the fixed bed is heated to 350° C., nitrogen is introduced steadily for 30 min. The methanol solution of formaldehyde prepared above is mixed with methyl propionate (the raw material molar ratio: methyl propionate/formaldehyde/methanol/water=58/21/20/1). The duration that the reactant contacts the catalyst is 5 s, twice of the flow rate of the liquid reaction of the toluene is fed from the bottom of the fixed bed. The product is cooled and separated for isolating the liquid product, the gas phase was evacuated after online mass spectrometry analysis.

After test and calculation, the conversion of methyl propionate is 23%; the prepared MMA has a selectivity of 91%; the selectivity of methyl propionate hydrolysis to propionic acid is 8%.

Example 3

The operation is the same as Example 2, except modifying the feed amount of the inert substance toluene to one time the volume of liquid reactant feed flow.

After test and calculation, the conversion of methyl propionate is 23%; the prepared MMA has a selectivity of 89%; and the selectivity of methyl propionate hydrolysis to propionic acid is 7.9%.

Example 4

The operation is the same as Example 2, except modifying the inert substance to n-heptane, the feed volume is twice the volume of the liquid reactant feed flow.

After test and calculation, the conversion of methyl propionate is 23%; the prepared MMA has a selectivity of 92.5%; and the selectivity of methyl propionate hydrolysis to propionic acid is 7.4%.

Example 5

The operation is the same as Example 2, except modifying the inert substance to n-hexane, the feed volume is twice the volume of the liquid reactant feed flow.

After test and calculation, the conversion of methyl propionate is 23%; the prepared MMA has a selectivity of 92.3%; and the selectivity of methyl propionate hydrolysis to propionic acid is 7.6%.

Example 6

The operation is the same as Example 2, except modifying the inert substance to xylene, the feed volume is twice the volume of the liquid reactant feed flow.

After test and calculation, the conversion of methyl propionate is 23%; the prepared MMA has a selectivity of 91.5%; the selectivity of methyl propionate hydrolysis to propionic acid is 8.2%.

Example 7

The operation is the same as Example 2, except modifying the inert substance to methanol, the feed volume is twice the volume of the liquid reactant feed flow.

After test and calculation, the conversion rate of methyl propionate is 23%; the prepared MMA has a selectivity of 90.2%; the selectivity of methyl propionate hydrolysis to propionic acid is 8.9%.

Comparative Example 1

Other operating processes are the same as Example 2, the only difference lies in that the bottom material is not flushed.

After test and calculation, the conversion of methyl propionate is 23%; the prepared MMA has a selectivity of 78%; the selectivity of methyl propionate hydrolysis to propionic acid is 8%. It is can be seen from the above examples and comparative example, under the same preparation operating conditions, the conversions of methyl propionate are same, but by the inert substances cooling down of the present application, the selectivity of the target product MMA is increased by more than 10%.

The embodiments of the present invention have been described above. However, this invention is not limited to the above embodiments. Any modifications, equivalent replacements, or improvements made within the spirit and principle of the present invention shall be included in the protection scope of the present invention.

The invention claimed is:

1. A method for improving reaction yield, comprising:
    feeding a raw material feedstock into a fixed bed reactor;
    contacting the raw material feedstock and a catalyst bed in the fixed bed reactor to produce a reaction product stream;
    passing the reaction product stream successively through, a space formed by the catalyst cushion and a reactor head, and an outlet of the fixed bed reactor;
    injecting an inert substance into the catalyst cushion,
    wherein the reaction product stream comprises heat sensitive compounds selected from vinyl acetate, acrylic acid, methacrylic acid, acrylate, methacrylate, methyl methacrylate, ethylenically unsaturated aldehyde, acrolein, methacrolein, propylene, isobutylene, butadiene, and styrene compounds, ethylene oxide, and propylene oxide, and
    wherein the catalyst cushion is a layer of packing material selected from ceramic, glass, and quartz.

2. The method according to claim 1, wherein the inert substance is at least one of a gas or a liquid that can be vaporized after being heated.

3. The method according to claim 1, wherein the inert substance is selected from nitrogen, helium, argon, carbon dioxide, water, oxygenated organics with a carbon number less than or equal to 10, nitrogenous organics with a carbon number less than or equal to 10, naphthene with a carbon number less than or equal to 12, alkanes with a carbon number less than or equal to 12, aromatics with a carbon number less than or equal to 10, or a mixture thereof.

4. The method according to claim 3, wherein the inert substance is selected from nitrogen, helium, argon, carbon dioxide, water, $C_6$-$C_8$ alkane, $C_6$-$C_8$ aromatic, $C_1$-$C_4$ alcohol, $C_1$-$C_4$ acid, $C_2$-$C_4$ nitrile, $C_2$-$C_4$ ester, hexane, heptane, benzene, toluene, xylene, methanol, ethanol, propionic acid, methyl propionate, and acetonitrile.

5. The method according to claim 1, wherein the inert substance is injected into the catalyst cushion through a nozzle.

6. The method according to claim 1, wherein a weight of the inert substance injected is 0.1-5 times a weight of the feedstock.

7. The method according to claim 1, wherein the raw material feedstock comprises at least one of olefins, alkanes, aromatic hydrocarbons, carboxylic acids, carboxylic acid esters, aldehydes, alcohols, ethylene, propylene, isobutylene, propane, butane, isobutane, acetic acid, propionic acid, methyl acetate, methyl propionate, formaldehyde, vinylaldehyde, acrolein, methacrolein, methanol, butene-1, phenylethanol, and ethylbenzene.

8. The method according to claim 6, wherein the weight of the inert substance injected is 0.5-2 times the weight of the raw material feedstock.

* * * * *